United States Patent
Harris et al.

(10) Patent No.: US 11,977,138 B2
(45) Date of Patent: *May 7, 2024

(54) SYSTEM AND METHOD FOR USING COILS IN MAGNETIC RESONANCE IMAGING

(71) Applicant: Synaptive Medical Inc., Toronto (CA)

(72) Inventors: Chad Tyler Harris, Toronto (CA); Geron André Bindseil, Toronto (CA)

(73) Assignee: Synaptive Medical Inc.

( * ) Notice: Subject to any disclaimer, the term of this patent is extended or adjusted under 35 U.S.C. 154(b) by 445 days.

This patent is subject to a terminal disclaimer.

(21) Appl. No.: 17/174,849

(22) Filed: Feb. 12, 2021

(65) Prior Publication Data
US 2021/0286031 A1  Sep. 16, 2021

Related U.S. Application Data

(63) Continuation of application No. 15/604,952, filed on May 25, 2017, now Pat. No. 10,921,398.

(51) Int. Cl.
*A61B 5/00* (2006.01)
*G01R 33/34* (2006.01)
(Continued)

(52) U.S. Cl.
CPC ...... *G01R 33/34084* (2013.01); *A61B 5/7217* (2013.01); *G01R 33/3657* (2013.01);
(Continued)

(58) Field of Classification Search
CPC .......... G01R 33/34084; G01R 33/3657; G01R 33/3875; G01R 33/5616; G01R 33/56341;
(Continued)

(56) References Cited

U.S. PATENT DOCUMENTS 9,322,891 B2  4/2016  Biber
9,541,619 B2  1/2017  Biber
(Continued)

FOREIGN PATENT DOCUMENTS

EP  0547917  6/1996

OTHER PUBLICATIONS

Office Action issued by the Canadian Intellectual Property Office in relation to corresponding Canadian Application No. 3,005,584 dated Mar. 21, 2019, 3 pages.
(Continued)

*Primary Examiner* — Joel Lamprecht (57) ABSTRACT

Some implementations provide an MRI system that includes: a housing having a bore accommodating a portion of a subject; a main magnet enclosed by said housing and configured to generate a substantially uniform magnet field within the bore; a gradient sub-system to provide perturbations to the substantially uniform magnet field; a flexible coil assembly configured to (i) receive radio frequency (RF) signals from the subject in response to the portion of the subject being scanned, and (ii) generate and apply $B_0$ shimming to improve a field homogeneity of the substantially uniform magnetic field; and a control unit configured to: drive the gradient sub-system using a gradient waveform; and receive measurement results responsive to the gradient waveform such that a coupling between the gradient sub-system and the flexible coil assembly is determined and subsequently reduced in response to the determined coupling exceeding a pre-determined threshold.

20 Claims, 4 Drawing Sheets

(51) Int. Cl.
  *G01R 33/36* (2006.01)
  *A61B 5/055* (2006.01)
  *G01R 33/3875* (2006.01)
  *G01R 33/561* (2006.01)
  *G01R 33/563* (2006.01)

(52) U.S. Cl.
  CPC .......... *A61B 5/055* (2013.01); *G01R 33/3875* (2013.01); *G01R 33/5616* (2013.01); *G01R 33/56341* (2013.01); *G01R 33/56366* (2013.01)

(58) Field of Classification Search
  CPC ........ G01R 33/56366; G01R 33/34076; G01R 33/3642; A61B 5/7217; A61B 5/055
  See application file for complete search history.

(56) References Cited

U.S. PATENT DOCUMENTS

| | | | |
|---|---|---|---|
| 10,921,398 B2* | 2/2021 | Harris | G01R 33/3657 |
| 2012/0323113 A1 | 12/2012 | Biber | |
| 2013/0193968 A1 | 8/2013 | Biber | |
| 2018/0340992 A1 | 11/2018 | Harris et al. | |

OTHER PUBLICATIONS

Search Report issued by UK Intellectual Property Office in relation to corresponding GB Application No. GB1808074.7 dated Dec. 7, 2018, 3 pages.

Truong, T-K. et al., "Integrated RF/shim coil array for parallel reception and localized B0 shimming in the human brain," NeuroImage, vol. 103, Dec. 2014, pp. 235-240.

* cited by examiner

SYSTEM AND METHOD FOR USING COILS IN MAGNETIC RESONANCE IMAGING

BACKGROUND

The present disclosure relates to magnetic resonance imaging.

SUMMARY

In one aspect, some implementations provide an MRI system that includes: a housing having a bore sized and shaped to exclusively accommodate a portion of a subject to be imaged; a main magnet enclosed by said housing and configured to generate a substantially uniform magnet field within the bore; a gradient sub-system comprising gradient coils to apply a gradient waveform that provides a magnetic field gradient as perturbations to the substantially uniform magnet field; a flexible coil assembly configured to (i) receive radio frequency (RF) signals from the subject in response to a portion of the subject being scanned, and (ii) generate and apply $B_0$ shimming to improve a field homogeneity of the substantially uniform magnetic field encompassing the portion of the subject being scanned; and a control unit configured to: drive the gradient sub-system using a gradient waveform; and receive measurement results responsive to the gradient waveform such that a coupling between the gradient sub-system and the flexible coil assembly is determined and subsequently reduced in response to the determined coupling exceeding a pre-determined threshold.

Implementations may include one or more of the following features.

The portion of the subject may include a head of the subject.

The flexible coil assembly may be shaped and sized to wrap around the portion of the subject. The flexible coil assembly may be coupled to a direct current (DC) power supply such that a DC current flows in the flexible coil assembly to generate and apply $B_0$ shimming to the substantially uniform magnetic field. The gradient coils may provide perturbations to the substantially uniform magnet field in more than one gradient axes.

The control unit may be configured to drive the gradient sub-system using a gradient waveform on each gradient axis. The control unit is configured to drive each gradient coil of the gradient subsystem individually using the gradient waveform when measurement results are received responsive to the gradient waveform. The control unit is configured to: in response to the coupling between the gradient sub-system and a particular coil from the flexible coil assembly being determined as larger than a pre-determined threshold, selectively turn off a direct current (DC) component of particular coil of the flexible coil assembly when the gradient waveform is being applied to generate the magnetic field gradient in tandem with the sequence of RF pulses during an MRI scan to acquire radio frequency (RF) signals from the portion of the subject. The sequence of RF pulses may include an echo-planar imaging (EPI) sequence, a perfusion-weighted sequence, or a diffusion-weighted sequence.

The measurements results may be used in a parametric model describing the coupling between the gradient sub-system and the flexible coil assembly such that the coupling is numerically determined.

In another aspect, some implementations provide a method that includes: placing a portion of a subject to be imaged inside a bore of a main magnet configured to generate a substantially uniform magnet field within the bore; wrapping a flexible coil assembly around the portion of the subject, the flexible coil assembly configured to (i) receive radio frequency (RF) signals from the subject in response to a portion of the subject being scanned, and (ii) generate and apply shimming to improve a field homogeneity of the substantially uniform magnetic field encompassing the portion of the subject being scanned; and operating a control unit such that a gradient sub-system is driven using a gradient waveform, and measurement results are received responsive to the gradient waveform such that a coupling between the gradient sub-system and the flexible coil assembly is determined and subsequently reduced in response to the determined coupling exceeding a pre-determined threshold.

Implementations may include one or more of the following features.

Placing a portion of the subject may include placing a head of the subject into the bore. The gradient coils may provide perturbations to the substantially uniform magnet field in more than one gradient axes; and wherein the gradient sub-system is driven using a gradient waveform on each gradient axis. Each gradient coil of the gradient sub-system may be driven individually using the gradient waveform when measurement results are received responsive to the gradient waveform.

The method may further include: in response to the coupling between the gradient sub-system and a particular coil from the flexible coil assembly being determined as larger than a pre-determined threshold, repositioning the flexible coil assembly such that the coupling is reduced or a direct current (DC) component of particular coil of the flexible coil assembly is selectively turned off when the gradient waveform is being applied to generate a magnetic field gradient in tandem with the sequence of RF pulses during an MRI scan to acquire radio frequency (RF) signals from the portion of the subject.

The imaging sequence may include an echo-planar imaging (EPI) sequence, a perfusion-weighted sequence, or a diffusion-weighted sequence. The coupling may be determined during a pre-scan before the imaging sequence is run. Feeding the measurements results to a parametric model describing the coupling between the gradient sub-system and the flexible coil assembly such that the coupling is numerically determined.

The details of one or more aspects of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Embodiments will now be described, by way of example only, with reference to the drawings, in which.

Like reference symbols in the various drawings indicate like elements.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

Integrated radiofrequency and shim (RF/shim) coil arrays can be used in magnetic resonance (MR) imaging to perform parallel reception and localized magnetic field shimming with the same coils in order to maximize the $B_0$ shimming efficiency and the signal-to-noise ratio (SNR) of MR signal acquisition. For example, magnetic susceptibility differences at air-tissue interfaces induce macroscopic static magnetic field inhomogeneities can often cause image artifacts such as distortion, blurring, and/or signal loss. To reduce such magnetic field inhomogeneities, coil designs in which a radiofrequency (RF) current and a direct current (DC) flow in the same coil simultaneously enables parallel RF excitation/reception and localized magnetic field shimming within a single coil array.

However, while integrated RF/shim coil designs can potentially improve SNR and shimming performance in whole-body MR systems, their use in MR systems where gradient coils are located physically closer to RF coils or where gradient coils are operated with very strong gradient fields can cause unwanted magnetic coupling between the gradient coils and the integrated RF/shim coils. This results in performance impediments, namely the generation of an incorrect field basis that is used to estimate optimal amplitudes for shimming coils. Additional safety concerns may unfold both for the patient and the MR hardware. As an example, if an integrated RF/shim coil array is arranged in close proximity to gradient coils (e.g., as in head-only MRI systems), then the current flow through the integrated RF/shim coil array may degrade image quality. In another example, if an MR system includes the use of flexible RF coils conforming to a shape of a subject area to be imaged, or if RF coils are incorrectly arranged (e.g., due to operator error, or due to a large size of the subject), then coupling between the integrated RF/shim coil array and the gradient coils can be more pronounced.

According to selected embodiments of the present disclosure, MR imaging systems and techniques are provided to measure and reduce coupling between an integrated RF/shim coil array and gradient coils of MR systems. A pre-scan procedure may be performed to detect and/or remove unwanted electrical coupling between an integrated RF/shim coil and gradient coils of an MR system. The pre-scan procedure may be performed to either measure an amount of coupling along each gradient axis, measure a location or orientation of the integrated RF/shim coil within the inner bore of the MR system, or both. The measurements collected during the pre-scan operation can then be adjusted to improve $B_0$ shimming generated and applied by the integrated RF/shim coil to improve the field homogeneity of the substantially uniform magnetic field. A determination can be reached as to whether or not the current orientation is safe. If not, the operator of the MR scan may be alerted so that the position and/or orientation may be adjusted.

During the pre-scan procedure, coupling along the gradient axis between the gradient coils and the integrated RF/shim coil may be measured using different approaches. In some instances, each gradient axis is pulsed or driven with some current waveform and the back electromotive forces (EMF) that are induced on the loops of the integrated RF/shim coils for each gradient axis as a result of the pulsation are measured as the coupling. In other instances, a computational model of the gradient coils and the orientation of the integrated RF/shim coil is used to model the interaction between the two, which is then used to predict the coupling.

The pre-scan procedure described throughout this specification enables MR systems where gradient coils are placed in close proximity to integrated RF/shim coils to overcome the limitations described above. In some instances, after the pre-scan procedure is performed, measurements of the coupling between the gradient coils and the RF/shim coils can be used to selectively disable loops of the integrated RF/shim coil along gradient axis for which the coupling is measured to exceed a predetermined threshold. In this regard, various types of adjustments can be made to reduce potential coupling between the gradient coils and the integrated RF/shim coil in order to overall improve image quality.

In addition, in some instances the orientation of the integrated RF/shim coil is measured during the pre-scan operation. In such instances, if the integrated RF/shim coil is determined to be placed in an incorrect orientation, the integrated RF/shim coil can be used to selectively disable certain coil elements during an MR sequence to reduce imaging errors or artifacts. Alternatively, the field profile of the loops of the integrated RF/shim coil assembly in the determined orientation can be calculated and a new field profile can be included in a shim optimization sequence.

Figure 1A:
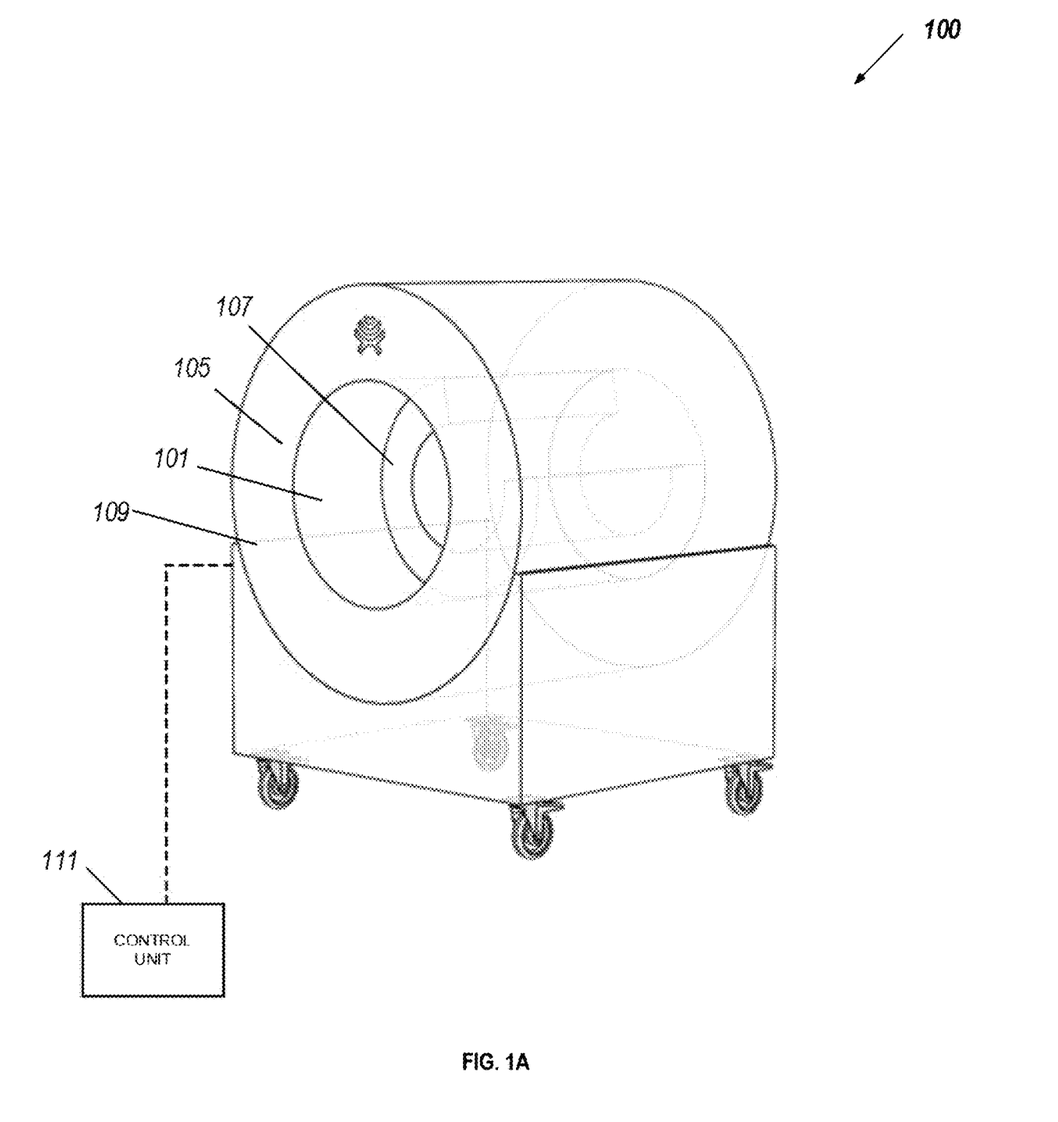
FIGS. 1A-1B show examples of a magnetic resonance imaging (MRI) system that is capable of incorporating an integrated RF/shim coil array.
Figure 1B:
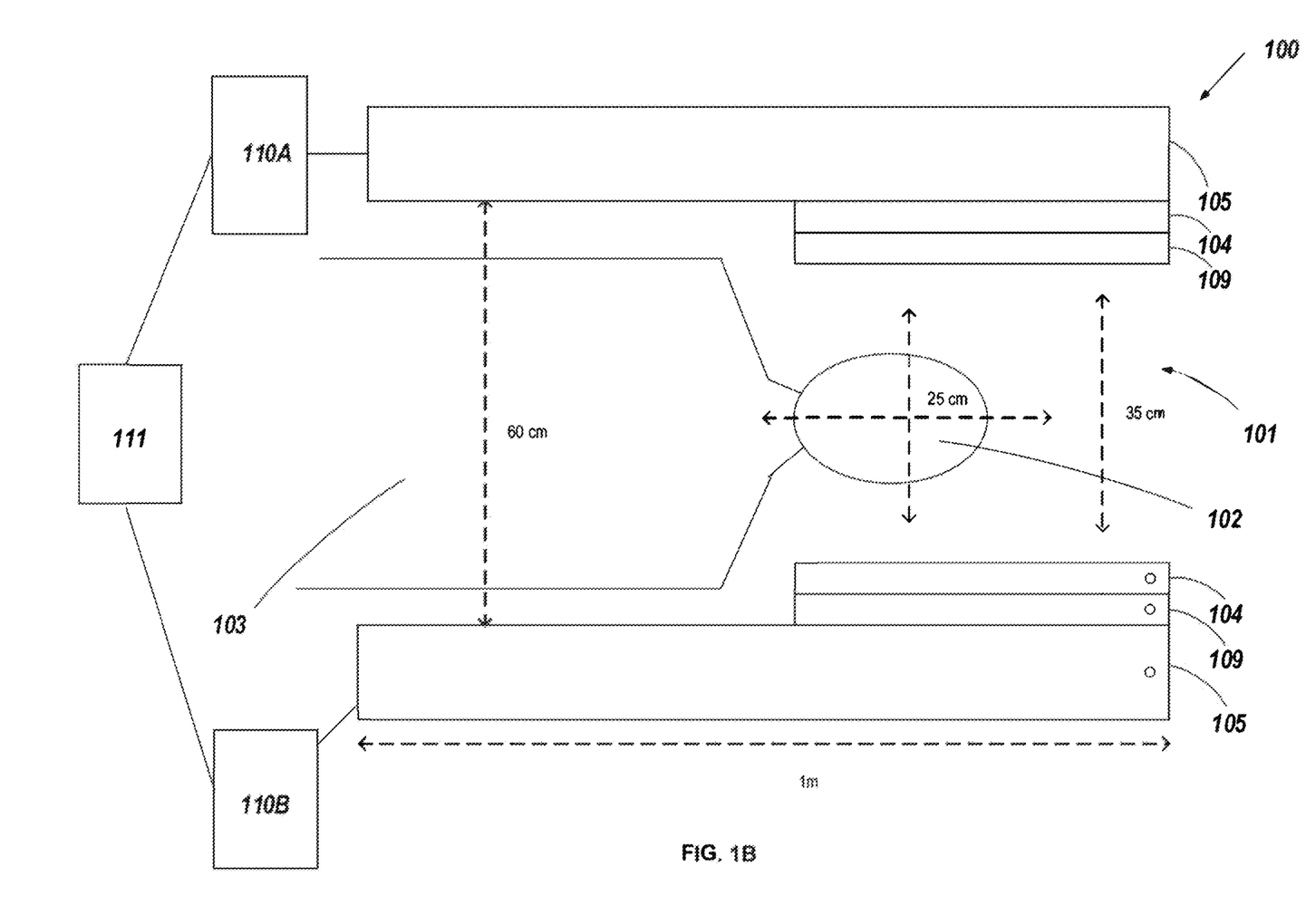

FIGS. 1A-1B show a perspective view and a top view, respectively, of an example of a magnetic resonance imaging (MRI) system 100 in which a solenoid magnet 105 is provided in a cylindrical shape with an inner bore 101.

For context, the solenoid magnet 105 of the MRI system 100 generates a highly-uniform static magnetic field over a certain volume for imaging purposes. Although small static field variations on the order of parts per million (ppm) can be tolerated, it is not possible to generate MR data in locations where the main field deviates too greatly (e.g., over hundreds of parts per million (ppm) over a 20 centimeter diameter spherical volume). For example, 40 ppm over a 25-cm diameter spherical volume (DSV) can represent a maximum $\Delta B0=B0\ max-B0\ min=20\ \mu T$ field deviation at a static field of $B0=0.5\ T$.

The solenoid magnet 105 is designed to achieve a specific homogeneity (that is, the main magnet is designed to have an inhomogeneity below a given threshold). However, the actual homogeneity at the installation site may be affected by material in or around the MRI scanner. At the time of installation, passive and/or active shim coils (e.g., the shim coils 109 and/or the gradient coils 104) may be applied to improve the homogeneity so that it meets the specific homogeneity the main magnet is designed to achieve before and/or after subjects are placed in the inner bore 101.

Gradient coils 104 generally provide gradient fields in one or more directions such as, for example, in three orthogonal spatial directions. Thus, the gradient coils 104 may refer to three sets of coils, each configured to generate field fluctuations in a respective direction for the magnetic field produced by the solenoid magnet 105 within the inner bore 101. Such field fluctuations may cause magnetizations from various spatial locations to experience precessions at different frequencies, enabling encoding of spatial information of the magnetizations through RF excitation pulses.

A flexible coil array 107 (also referred to as an "integrated RF/shim coil") is provided within solenoid magnet 105. For simplicity of illustration, block 107 is shown in a cylindrical appearance. But, flexible coil 107 would not assume the shape of rigid tubes. The flexible coil array 107 is capable of being shaped and sized to wrap around a portion of the subject that is placed within the inner bore 101. The coil array 107 includes coils for receiving radio frequency (RF) signals in a sequence to scan the portion of the subject, and applying $B_0$ shimming to improve field homogeneity of the magnetic field produced by the solenoid magnet 105. Notably, the coil array 107 may not be involved in generating RF pulses. In this way, the coil array 107 can include a single device that is capable of performing parallel reception and localized magnetic field shimming with the same coils to maximize both the SNR and the $B_0$-shimming efficiency during an imaging operation. In some instances, the coil array 107 is generally shaped as an annular structure and housed within the inner bore of solenoid magnet 105.

In one instance, a head coil in a birdcage configuration is used for both transmitting and receiving RF signals for imaging the subject. In another instance, a transmit RF coil would excite the signal and a receiver RF coil would receive the signal, wherein the receiver RF coil can be a single coil or a phased array. The embodiments provided herein may be adapted for intraoperative MRI, and MRI systems for use in an emergency room setting.

In various instances, $B_0$-shimming coils 109 are housed within the cylindrical walls of the gradient system. The $B_0$-shimming coils 109 are powered by a group of power amplifiers. For example, power amplifiers housed in a control room may be connected to $B_0$-shimming coils 109 to provide shimming of the magnetic field within inner bore 101. In driving shimming coils 109, power amplifiers may be controlled by a control unit 111. Within the confines of this disclosure, the $B_0$ shimming coils are integrated with the flexible coil array 107.

The control unit 111 generally includes one or more processors as well as programming logic to configure the power amplifier and perform other operations explained in more detail below. In some instances, control unit 111 is housed in a control room separate from the solenoid magnet 105 of the MRI system 100. In these implementations, an array of shimming coils can be used to provide adjustment to the field strength within the inner bore 101 such that the magnet field within the inner bore 101 becomes more homogenous, as explained in more detail below.

The control unit 111 can be used to drive the gradient coils outside the coil array 107 using gradient waveforms. In some instances, the control unit 111 can provide gradient waveforms along each gradient axis such that the gradient coils corresponding to each axis are selectively driven to perturb the magnetic field generated within the inner bore 101 along a specified axis. The control unit 111 can then be used to obtain measurement results responsive to the application of gradient waveforms such that coupling between the gradient coils 104 and the coil array 107 (as an integrated RF/shim coil) is determined. As discussed in more detail below, the measurements results can be factored into generating and applying B0-shimming using the B0-shimming coils 109 and/or the coil array 107 to improve the magnetic field homogeneity within the inner bore 105.

The control unit 111 can also be used to manually or automatically adjust the operation of the MRI system 100 to reduce or remove coupling between the gradient coils 104 and the coil array 107. In some instances, the control unit 111 may automatically compare the measured coupling between the gradient coils 104 and the coil array 107 to a predetermined threshold, and in response to determining that the measured coupling exceeds the predetermined threshold, the control unit 111 may execute instructions to selectively disable a particular DC coil element in the RF/shim coil when a gradient waveform is being applied to generate a magnetic field gradient in tandem with a sequence of RF pulses during an MRI scan to acquire RF signals from the portion of the subject within the inner bore 105. In some instances, the adjustments to the operation of the MRI system 100 may be performed manually by an operator that uses the control unit 111. In such instances, the measurement results relating to the coupling between the gradient coils 104 and the coil array 107 may be presented on a user interface of the control unit 111. The operator may then receive different options to adjust the operation of individual coils to reduce or remove the measured coupling.

Figure 2:
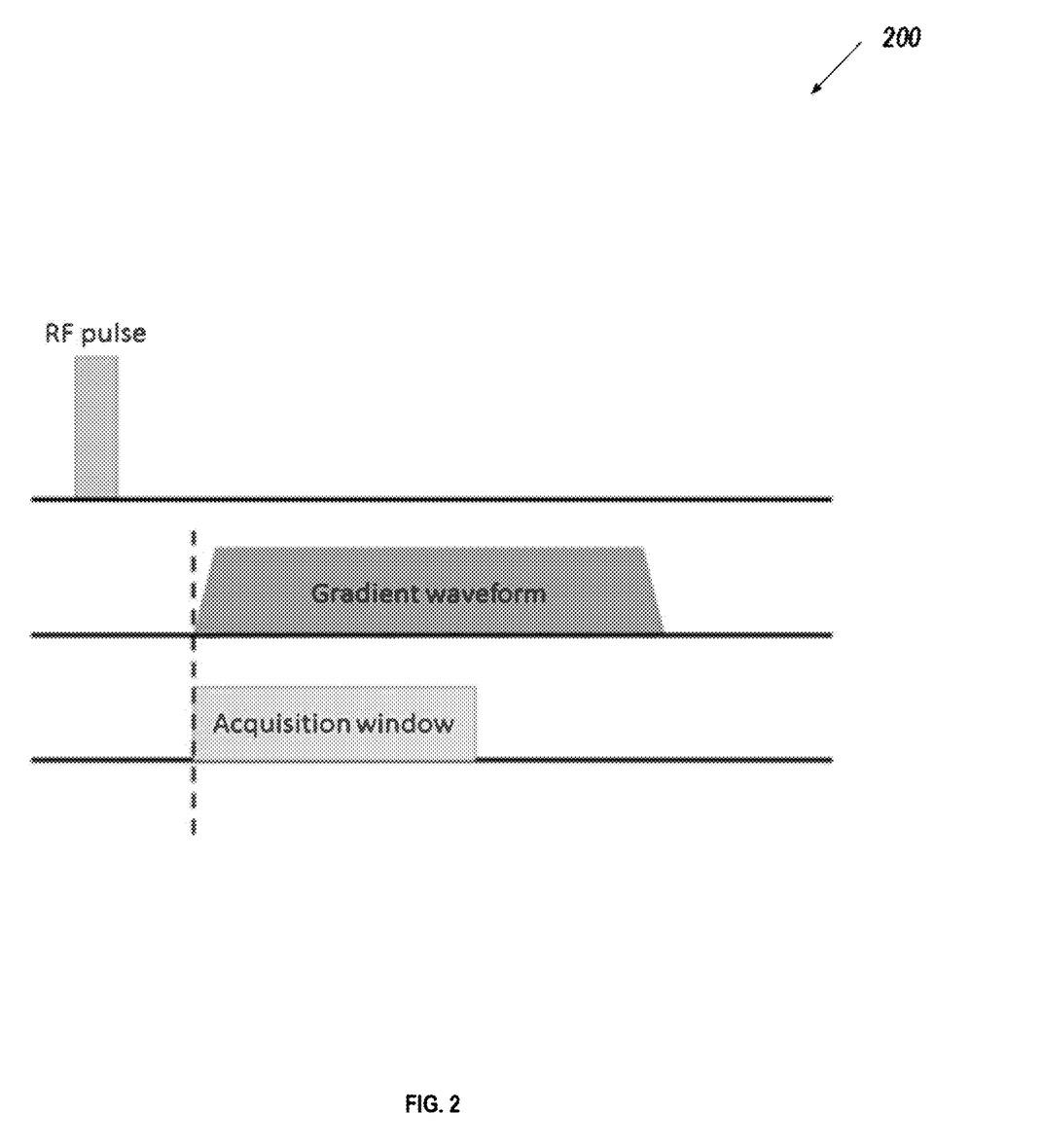
FIG. 2 shows an example of an acquisition sequence for measuring coupling between RF and shim coils.

FIG. 2 shows an example of an acquisition sequence 200 for measuring coupling between the gradient coils and the integrated RF/shim coil array. The acquisition sequence 200 is generally performed as a calibration scan prior to performing an imaging procedure. The acquisition sequence 200 enables measurement of an amount of undesired coupling between gradient coils and the RF/shim coil assembly 107 when a low frequency current pathway is passed through the RF loop of the coil assembly 107. As discussed above, the passing of the low frequency current pathway enables the coil assembly 107 to function as both local transmit and/or receive coils as well as function as a $B_0$-shim coil to improve field homogeneity of the magnetic field generated within the inner bore 101.

Various techniques can be used to identify coupling between the gradient coils and the RF/shim coils within the coil assembly 107.

Additionally, or alternatively, in other implementations, the coupling between the gradient coils and the RF coils within the coil assembly 107 is measured using a finite-element (FE) model that describe discrete properties of the gradient coils using a set of parameters. In such implementations, numerical values for each parameter are measured and used to characterize the interactions between the gradient coils and the RF coils within the coil assembly 107. For example, the FE model can be developed based on the dimensional design specifications of the gradient coils and the concentration of copper windings in the coil and used to represent vibration, acoustic noise, and/or conductance properties of the gradient coils. The FE model is then validated using experimentally collected data for the gradient coils. Using a predicted orientation of the RF coils of the coil assembly and the frequency of the current run through the gradient coils, the FE model can then be used to estimate a coupling between gradient coils and the RF coils of the coil assembly 107.

In some implementations, the amount of coupling may be measured along each gradient axis of the coil assembly 107 (e.g., x-axis, y-axis, and/or z-axis). In such implementations, the control unit 111 is configured to generate respective gradient waveforms for each axial gradient coil to generate gradient fields along each axis. In this regard, the application of gradient waveform along each axis and measurement of the induced electromagnetic fields along the corresponding axial gradient coils can be used to measure coupling along each axis of the gradient coils within the coil assembly 107.

To identify a position and/or orientation of the RF coils within the coil assembly 107, one or more magnetic field measuring devices (e.g., multiaxial hall probes) can be attached to the surface of the RF coils. Field measurements of the RF coils are then taken when gradient pulses are applied to each individual gradient coil within the coil assembly 107 as described above. In this regard, collected field measurements can be used to indicate a current location and orientation of the measuring devices, which then corresponds to the current location and the orientation of the RF coils attached to them. In some implementations, the position and/or orientation of the RF coils are determined through fiducial markers visible in MRI images acquired by a larger RF coil (for example, a large transmit and receive birdcage coil placed outside of RF coil array 107).

Figure 3A:
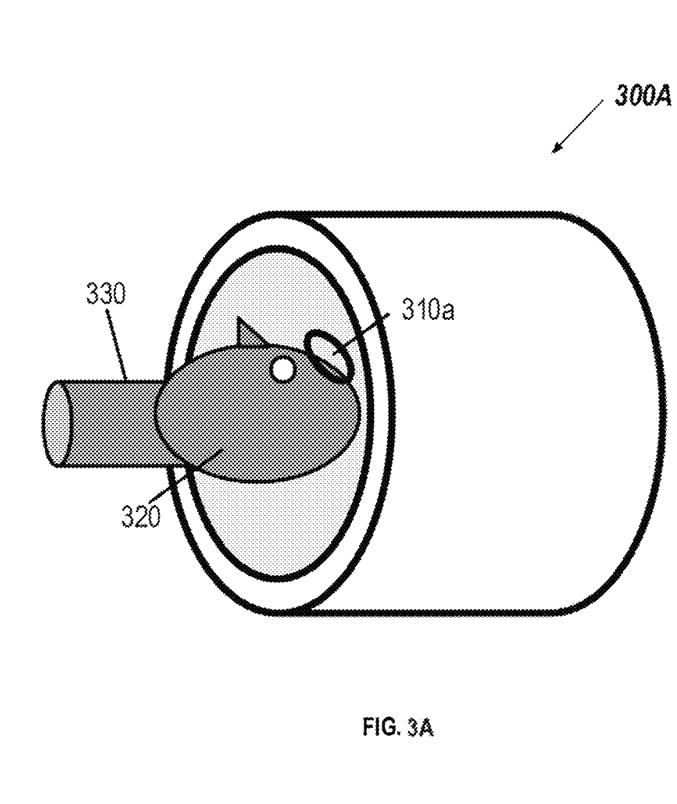
FIGS. 3A-3B show examples of different RF loop orientations produced during a head-only MRI imaging sequence.
Figure 3B:
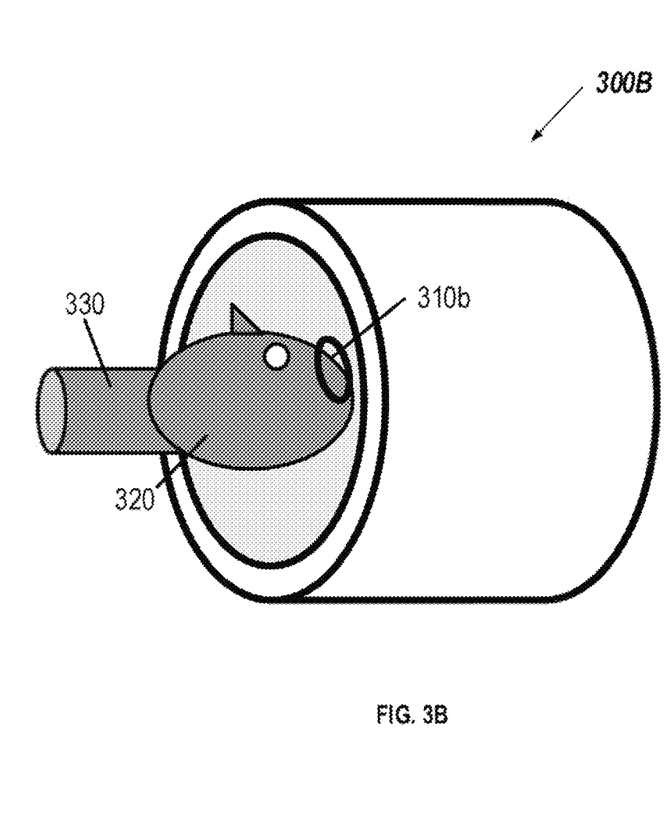

FIGS. 3A-3B show examples of different RF loop orientations produced during a head-only MRI imaging sequence. Referring initially to FIG. 3A, a single RF coil loop element in the flexible coil array 107 is shown in a particular orientation 310a and is produced during a head-only MR imaging procedure 300A of a subject's head 320. In this example, the RF loop orientation 310a is an incorrect orientation that is generated as result of, for example, coupling between the gradient coils 104 and the flexible coil array 107, an incorrect orientation of the flexible coil array 107, or both.

A pre-scan operation, as described above, is then performed to measure the coupling between the gradient coils 104 and the flexible coil array 107 and/or the orientation of the flexible coil array 107 during the MR imaging procedure 300A. The measured coupling and/or orientation can then be factored into generating and applying a subsequent $B_0$ shimming signal that removes the particular RF loop 310a from use in the $B_0$ shimming signal during the operation of the gradient coil during the MRI imaging sequence. In an alternative implementation, if the position of the RF loop 310a is inappropriate for coupling with the gradient coil, the imaging system control unit 111 may inform the operator to change the orientation of RF loop 310a and repeat the pre-scan operation until an orientation of RF loop 310a is found such that the coupling is below a certain threshold.

Referring now to FIG. 3b, after the pre-scan operation is performed, B0-shimming is then generated and applied during a head-only MR imaging procedure 300B of the subject's head 320. In one instance, the RF loop orientation 310b represents the correct orientation because a change in location and orientation has been applied to substantially remove the coupling between the gradient coils 104 and the flexible coil array 107 and any resulting distortions.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A magnetic resonance imaging (MRI) system, comprising:
    a main magnet configured to generate a substantially uniform magnet field over a portion of a subject;
    a gradient sub-system comprising a plurality of gradient coils;
    an integrated radio frequency and shim (RF/Shim) flexible coil assembly comprising at least one RF coil, each at least one RF coil configured to:
        receive radio frequency (RF) signals from the subject in response to the portion of the subject being imaged by the MRI system, and
        generate and apply $B_0$ shimming to improve a field homogeneity of the substantially uniform magnetic field when the portion of the subject is being imaged; and
    a control unit configured to:
        determine a coupling between each gradient coil of the gradient sub-system and each at least one RF coil of the integrated radio frequency and shim (RF/Shim) flexible coil assembly; and
        allow an adjustment to the at least one RF coil of the integrated radio frequency and shim (RF/Shim) flexible coil assembly when the coupling exceeds a pre-determined threshold.

2. The MRI system of claim 1, wherein the control unit is further configured to determine the coupling by:
    driving each gradient coil of the gradient sub-system individually using a gradient waveform; and
    receiving measurement results responsive to the gradient waveform, wherein the measurement results indicate the coupling.

3. The MRI system of claim 2, wherein the control unit is configured to, in response to determining that the coupling between the gradient sub-system and a particular coil from the integrated radio frequency and shim (RF/Shim) flexible coil assembly exceeds the pre-determined threshold, selectively turn off a direct current (DC) component of particular coil of the integrated radio frequency and shim (RF/Shim) flexible coil assembly when the gradient waveform is being applied in tandem with a sequence of RF pulses during an MRI scan to acquire radio frequency (RF) signals from the portion of the subject.

4. The MRI system of claim 3, wherein the sequence of RF pulses includes an echo-planar imaging (EPI) sequence, a perfusion-weighted sequence, or a diffusion-weighted sequence.

5. The MRI system of claim 2, wherein the measurements results are used in a parametric model describing the coupling between the gradient sub-system and the integrated radio frequency and shim (RF/Shim) flexible coil assembly such that the coupling is numerically determined.

6. The MRI system of claim 1, wherein the control unit is further configured to, in response to determining that the coupling between the gradient sub-system and a particular coil of the integrated radio frequency and shim (RF/Shim) flexible coil exceeds the pre-determined threshold, generating an indication to an operator of the MRI system for the operator to reduce the coupling by adjusting the particular coil.

7. The MRI system of claim 1, wherein the portion of the subject includes a head of the subject.

8. The MRI system of claim 1, wherein the integrated radio frequency and shim (RF/Shim) flexible coil assembly is shaped and sized to wrap around the portion of the subject.

9. The MRI system of claim 1, wherein the integrated radio frequency and shim (RF/Shim) flexible coil assembly is coupled to a direct current (DC) power supply such that a DC current flows in the integrated radio frequency and shim (RF/Shim) flexible coil assembly to generate and apply $B_0$ shimming to the substantially uniform magnetic field.

10. The MRI system of claim 1, wherein the gradient coils provide perturbations to the substantially uniform magnet field in more than one gradient axes; and wherein the control unit is configured to drive the gradient sub-system using a gradient waveform on each gradient axis.

11. A method for operating a magnetic resonance imaging (MRI) system, the method comprising:
    placing a portion of a subject to be imaged inside a bore of a main magnet configured to generate a substantially uniform magnet field within the bore;
    wrapping an integrated radio frequency and shim (RF/Shim) flexible coil assembly around the portion of the subject, the integrated radio frequency and shim (RF/Shim) flexible coil assembly comprising at least one RF coil, each at least one RF coil configured to: receive radio frequency signals from the subject in response to the portion of the subject being scanned, and generate and apply $B_0$ shimming to improve a field homogeneity of the substantially uniform magnetic field encompassing the portion of the subject being scanned; and
    determining a coupling between each gradient coil of a gradient sub-system and each at least one RF coil of the integrated radio frequency and shim (RF/Shim) flexible coil assembly; and
    allowing an adjustment to the at least one RF coil of the integrated radio frequency and shim (RF/Shim) flexible coil assembly when the coupling exceeds a pre-determined threshold.

12. The method of claim 11, wherein determining the coupling comprises:
    driving each gradient coil of the gradient sub-system individually using a gradient waveform; and
    receiving measurement results responsive to the gradient waveform, wherein the measurement results indicate the coupling.

13. The method of claim 12, further comprising:
    in response to determining that the coupling between the gradient sub-system and a particular coil from the integrated radio frequency and shim (RF/Shim) flexible coil assembly exceeds the pre-determined threshold, selectively turn off a direct current (DC) component of particular coil of the integrated radio frequency and shim (RF/Shim) flexible coil assembly when the gradient waveform is being applied in tandem with a sequence of RF pulses during an MRI scan to acquire radio frequency (RF) signals from the portion of the subject.

14. The method of claim 13, wherein the sequence of RF pulses includes an echo-planar imaging (EPI) sequence, a perfusion-weighted sequence, or a diffusion-weighted sequence.

15. The method of claim 12, wherein the measurements results are used in a parametric model describing the coupling between the gradient sub-system and the integrated radio frequency and shim (RF/Shim) flexible coil assembly such that the coupling is numerically determined.

16. The method of claim 11, further comprising:
    in response to determining that the coupling between the gradient sub-system and a particular coil of the integrated radio frequency and shim (RF/Shim) flexible coil exceeds the pre-determined threshold, generating an indication to an operator of the MRI system for the operator to reduce the coupling by adjusting the particular coil.

17. The method of claim 11, wherein the portion of the subject includes a head of the subject.

18. The method of claim 11, wherein the integrated radio frequency and shim (RF/Shim) flexible coil assembly is shaped and sized to wrap around the portion of the subject.

19. The method of claim 11, wherein the integrated radio frequency and shim (RF/Shim) flexible coil assembly is coupled to a direct current (DC) power supply such that a DC current flows in the integrated radio frequency and shim (RF/Shim) flexible coil assembly to generate and apply B0 shimming to the substantially uniform magnetic field.

20. A method of fabricating a magnetic resonance imaging (MRI) system, comprising:
    providing a main magnet configured to generate a substantially uniform magnet field over a portion of a subject;
    providing a gradient sub-system comprising a plurality of gradient coils;
    providing an integrated radio frequency and shim (RF/Shim) flexible coil assembly comprising at least one RF coil, each at least one RF coil configured to:
        receive radio frequency (RF) signals from the subject in response to the portion of the subject being imaged by the MRI system, and
        generate and apply $B_0$ shimming to improve a field homogeneity of the substantially uniform magnetic field when the portion of the subject is being imaged; and
    providing a control unit configured to:
        determine a coupling between each gradient coil of the gradient sub-system and each at least one RF coil of the integrated radio frequency and shim (RF/Shim) flexible coil assembly; and
        allow an adjustment to the at least one RF coil of the integrated radio frequency and shim (RF/Shim) flexible coil assembly when the coupling exceeds a pre-determined threshold.

* * * * *